(12) United States Patent
Okumura

(10) Patent No.: US 10,863,953 B2
(45) Date of Patent: Dec. 15, 2020

(54) MOBILE X-RAY IMAGING DEVICE

(71) Applicant: SHIMADZU CORPORATION, Kyoto (JP)

(72) Inventor: Hiroshi Okumura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 245 days.

(21) Appl. No.: 16/305,893

(22) PCT Filed: Jun. 1, 2016

(86) PCT No.: PCT/JP2016/066115
§ 371 (c)(1),
(2) Date: Nov. 30, 2018

(87) PCT Pub. No.: WO2017/208379
PCT Pub. Date: Dec. 7, 2017

(65) Prior Publication Data
US 2020/0315561 A1    Oct. 8, 2020

(51) Int. Cl.
*A61B 6/00*    (2006.01)
*A61B 6/10*    (2006.01)
*G01N 23/04*    (2018.01)

(52) U.S. Cl.
CPC ........... *A61B 6/4405* (2013.01); *A61B 6/102* (2013.01); *A61B 6/461* (2013.01); *A61B 6/54* (2013.01); *A61B 6/56* (2013.01); *G01N 23/04* (2013.01); *G01N 2223/301* (2013.01)

(58) Field of Classification Search
CPC ......... A61B 6/4405; A61B 6/56; A61B 6/102; A61B 6/461; A61B 6/54; G01N 23/04; G01N 2223/301
USPC .......................................................... 378/62
See application file for complete search history.

(56) References Cited

FOREIGN PATENT DOCUMENTS

EP    0894472    2/1999
JP    2006239070    9/2006

OTHER PUBLICATIONS

"Search Report of Europe Counterpart Application", dated Jan. 2, 2020, p. 1-p. 6.
"Written Opinion of the International Searching Authority (Form PCT/ISA/237(Box No. V))" of PCT/JP2016/066115 , dated Aug. 16, 2016, with English translation thereof, pp. 1-3.
"International Search Report (Form PCT/ISA/210)" Of PCT/JP2016/066115, dated Aug. 16, 2016, with English translation thereof, pp. 1-2.

*Primary Examiner* — David P Porta
*Assistant Examiner* — Gisselle M Gutierrez
(74) *Attorney, Agent, or Firm* — JCIPRNET

(57) ABSTRACT

Provided inside a trolley are: a battery (1); a switchgear (2) arranged in a main path connecting a load (100) to the battery (1); a control circuit (7) controlling the load (100) and connected to the main path; a startup switch (4) opened and closed by operation of a key (29); and a startup circuit (5) that is connected to the battery (1) and activates the switchgear (2). Electric power supplied from the battery (1) to the startup circuit (5) and the control circuit (7) are respectively converted by a startup DC-DC converter (3) and a control DC-DC converter (6) to a voltage that activates the startup circuit (5) and the control circuit (7). When the device is in a sleep mode, electric power supply is received from the startup DC-DC converter (3) and a startup circuit connection relay (55) detects input from an operation switch (30) and operates.

7 Claims, 8 Drawing Sheets

MOBILE X-RAY IMAGING DEVICE

CROSS-REFERENCE TO RELATED APPLICATION

This application is a 371 application of the International PCT application serial no. PCT/JP2016/066115, filed on Jun. 1, 2016. The entirety of the above-mentioned patent application is hereby incorporated by reference herein and made a part of this specification.

BACKGROUND OF THE INVENTION

Technical Field

The disclosure relates to a mobile X-ray imaging device which performs an X-ray imaging with electric power charged into a battery.

Related Art

The mobile X-ray imaging device is equipped with elements on a trolley which is provided with wheels so as to move between hospital rooms, and the elements such as an X-ray tube supported by a support member or an X-ray detector like a flat panel detector perform various types of processing for X-ray imaging. In addition, such a mobile X-ray imaging device is equipped with a battery so that the X-ray imaging can be performed in unspecified locations including a case without external electric source (see patent literature 1).

In such a mobile X-ray imaging device which uses a battery as electric source, it is required to suppress power consumption of the battery so that a long time use is possible on a single charge to the battery. Therefore, a proposal is made that in a case that operation input from an operator is not detected for a fixed time when a power switch of the device is in an on state, the device is switched to a sleep mode with low power consumption.

LITERATURE OF RELATED ART

Patent Literature

Patent literature 1: Japanese Laid-open No. 2006-239070

SUMMARY

Problems to be Solved

FIG. 8 is a circuit diagram illustrating a main electrical structure of a conventional mobile X-ray imaging device.

A battery 1 is connected to a load 100 consuming electric power during X-ray imaging or to a control circuit 7 controlling the load 100. In addition, in a main path which supplies electric power from the battery 1 to the load 100 or the control circuit 7, a switchgear 2 is arranged. The switchgear 2 operates by a startup circuit 105 that is connected to the battery 1 when a startup switch 4 which is switched by operation of an operator when power source of the device is on/off is in a closing state. The switchgear 2 is in a closing state and electric power of voltage (for example, 15 V) converted via a control DC-DC converter 6 is supplied to the control circuit 7, thereby leading to an on state of the electric source of the device.

Since a voltage of the battery 1 is a large voltage (for example, 240 V), from the perspective of electric shock prevention of the operator, the switchgear 2 is configured to be activated via the startup circuit 105 when the battery 1 and the load 100 are connected. Electrical power from the battery 1 is supplied to the startup circuit 105 by the operator operating the startup switch 4. Electric power supplied to the startup circuit 105 has a voltage (for example, 12 V) lower than a voltage supplied to the control circuit 7 or the load 100 by a startup DC-DC converter 3. Furthermore, because the startup switch 4 is opened and closed by operation of the operator, a protection resistor 9 is disposed in a path from the battery 1 provided with the startup switch 4 to the startup circuit 105.

The startup circuit 105 is arranged with a two-winding latching relay 51 capable of self-holding, a capacitor 52, a switch 57 opened and closed by the latching relay 51, an opening-closing relay 53 that activates the switchgear 2 by the switch 5 being in a closing state, and a switch 58. A capacitor 52 is connected in series with respect to an unillustrated set coil of the latching relay 51. Besides, the switch 58 is connected in series with respect to an unillustrated reset coil of the latching relay 51. Furthermore, the switch 58 is opened and closed by a mode transition relay 54 and the mode transition relay 54 operates in accordance with a command signal from the control circuit 7.

If the startup switch 4 is closed by operation of the operator and electric power is supplied to the startup circuit 105, a charging current flows to the capacitor 52, and accordingly the set coil of the latching relay 51 operates and the switch 57 is in a closing state. Furthermore, the switch 58 is in an opening state at this time. In that case, the current flows to the opening-closing relay 53, and the switchgear 2 is in a closing state by operation of the opening-closing relay 53.

When the switchgear 2 is in the closing state, it comes into a normal startup mode in which electric power is supplied from the control circuit 7 or the load 100 to the battery 1. On the other hand, in a case that there is no operation input from the operator for a fixed time when the startup switch 4 is in a closing state, the switchgear 2 is set to the opening state and the transition to a sleep mode with low power consumption is realized. When signals from a plurality of operation switches connected to the control circuit 7 are not input to the control circuit 7 for a fixed time, the transition to sleep mode is performed by sending the signals from the control circuit 7 to the mode transition relay 54. According to the command signals from the control circuit 7, the mode transition relay 54 sets the switch 58 of the startup circuit 5 to the closing state. In this way, the switch 57 is in the opening state, electric power of the opening-closing relay 53 is lost, and the switchgear 2 is in the opening state. By setting the switchgear 2 to the opening state, connection of the battery 1 to the control circuit 7 and the load 100 is cut off and the device comes into the sleep mode. At this time, electric power is supplied to the startup circuit 105 and a state of extremely low power consumption is realized.

However, in the conventional mobile X-ray imaging device, the control circuit 7 also loses electric power when the device is in the transition to the sleep mode. Therefore, the mode transition relay 54 is activated by the control circuit 7 when the device is in the transition to the sleep mode, but the mode transition relay 54 or the startup circuit 105 cannot be activated by the control circuit 7 when the device is restored from the sleep mode to the normal startup mode. Therefore, conventionally, when the state of the device that is temporarily in the transition to the sleep mode is restored to normal startup mode, a restart operation is required in which the operator sets the startup switch 4 to the opening state and sets the startup switch 4 to the closing state again. Furthermore, immediately after the startup switch 4 is set to the opening state, electric power remains in the startup DC-DC converter 3. Therefore, the operator has to wait a few seconds for an operation that sets the startup switch 4 to the closing state until the startup DC-DC converter 3 and the startup circuit 5 completely lose electric power.

A circuit is also considered in which electric power is supplied to the control circuit 7 even in the sleep mode in order that the device is not restarted by the opening and closing of the startup switch 4 by operation of the operator. However, in this case, electric power is continuously supplied from the battery 1 to the control circuit 7 provided with a processor, and an effect of suppressing power consumption of the battery 1 is reduced.

The disclosure is accomplished to solve the above problems, and the first purpose is to provide a mobile X-ray imaging device which reduces consumed power of the battery in the sleep mode and can easily restore from the sleep mode to the normal startup mode of the device.

In addition, a status indicator for displaying a state of the device is connected to the control circuit 7. As described above, in the conventional mobile X-ray imaging device, the control circuit 7 also loses electric power when the device is in the transition to the sleep mode, so that display of the status indicator is also turned off. Therefore, there is an occasion in which it is difficult for the operator to determine whether the device is in the sleep mode or the startup switch 4 is in the opening state or the device has failed.

The disclosure is accomplished to solve the above problems, and the second purpose is to provide a mobile X-ray imaging device which can inform the operator that the device is in the sleep mode with low consumed power.

Means to Solve Problems

The invention recited in technical solution 1 is a mobile X-ray imaging device, on a moving trolley of which is equipped with an X-ray irradiation part having an X-ray tube for generating X-rays, an X-ray detector detecting the X-rays, a battery, and an electric power supply circuit for supplying electric power stored in the battery to a load. The mobile X-ray imaging device includes: a startup switch that opens and closes a supply path of electric power from the battery by operation of an operator; a switchgear arranged in a main path of electric power supply from the battery to the load; a startup circuit that has an opening-closing relay of the switchgear and sets the device to a normal startup mode by receiving the electric power supply from the battery and setting the switchgear to the closing state when the startup switch is in the closing state; a startup DC-DC converter converting a voltage of electric power supplied from the battery to a voltage that activates the startup circuit; a control circuit that receives the supply of electric power from the battery when the switchgear is in the closing state and that includes a processor calculating an operation signal of the device; a control DC-DC converter converting the voltage of electric power supplied from the battery to a voltage that activates the control circuit; a mode transition relay that changes an energization state of the opening-closing relay in the startup circuit according to a command of the control circuit after a fixed time has elapsed since the startup switch is in the closing state, thereby the switchgear is set to the opening state and the device is set to a sleep mode; an operation switch that is connected to the control circuit and that inputs an operation instruction to the device; and a startup circuit connection relay that detects input from the operation switch and operates by receiving the supply of electric power from the startup DC-DC converter through the startup circuit when the device is in the sleep mode. In a case that the startup circuit connection relay detects input of the operation switch and operates when the device is in the sleep mode, the startup circuit changes the energization state of the opening-closing relay again to set the switchgear to the closing state, and restores the device from the sleep mode to the normal startup mode.

The invention recited in technical solution 2 is the invention recited in technical solution 1, in which a status indicator for displaying a state of the device is connected to the control circuit, and the control circuit receives the supply of electric power through the startup DC-DC converter when the device is in the sleep mode and causes the status indicator to display that the device is in the sleep mode.

The invention recited in technical solution 3 is the invention recited in technical solution 2, in which the control circuit includes a timer IC, and controls display of the status indicator by the processor in the normal startup mode and controls display of the status indicator by the timer IC in the sleep mode.

The invention recited in technical solution 4 is the invention recited in technical solution 1, in which the startup circuit includes a two-winding latching relay and a capacitor connected in series to a set coil in the two-winding latching relay.

The invention recited in technical solution 5 is the invention recited in technical solution 1, in which the startup switch is a key operation switch in which a contact point is opened and closed by operation of a key.

The invention recited in technical solution 6 is the invention recited in technical solution 1, in which the operation switch includes any one of a brake lever arranged with an operation handle operating a traveling direction of the moving trolley, a release button releasing fixation of a collimator position in a collimator that specifies an X-ray irradiation field in the X-ray irradiation part, a lighting button of a collimator lamp for confirming the X-ray irradiation field specified by the collimator, and a bumper switch detecting that a bumper arranged on a front surface of the moving trolley collides with an obstacle.

The invention recited in technical solution 7 is a mobile X-ray imaging device, on a moving trolley of which is equipped with an X-ray irradiation part having an X-ray tube for generating X-rays, an X-ray detector detecting the X-rays, a battery, and an electric power supply circuit for supplying electric power stored in the battery to a load. The mobile X-ray imaging device includes: a startup switch that opens and closes a supply path of electric power from the battery by operation of an operator; a switchgear arranged in a main path of electric power supply from the battery to the load; a startup circuit that has an opening-closing relay of the switchgear and sets the device to a normal startup mode by receiving the electric power supply from the battery and setting the switchgear to the closing state when the startup switch is in the closing state; a startup DC-DC converter converting a voltage of electric power supplied from the battery to a voltage that activates the startup circuit; a mode transition relay that blocks energization to the opening-closing relay in the startup circuit after a fixed time has elapsed since the startup switch is in the closing state, thereby the switchgear is set to the opening state and the device is set to a sleep mode; and a startup circuit connection relay that operates by receiving the electric power supply from the startup DC-DC converter through the startup circuit when the device is in the sleep mode. In a case that the startup circuit connection relay detects input from an operation switch and operates when the device is in the sleep mode, the startup circuit restarts the energization to the opening-closing relay to set the switchgear to the closing state and restores the device from the sleep mode to the normal startup mode. The operation switch is any one of a brake lever arranged with an operation handle operating a traveling direction of the moving trolley, a release button releasing fixation of a collimator position in a collimator that specifies an X-ray irradiation field in the X-ray irradiation part, a lighting button of a collimator lamp for confirming the X-ray irradiation field specified by the collimator, and a bumper switch detecting that a bumper arranged on a front surface of the moving trolley collides with an obstacle.

Effect

According to the invention recited in technical solution 1 and technical solution 7, a path is provided which supplies electric power of the battery through the startup DC-DC converter to the startup circuit connection relay in the sleep mode, and input from the operation switch can be detected not only in the normal startup mode but also in the sleep mode. Therefore, an operator can easily perform a restoration operation that restores the device from the sleep mode to the normal startup mode by the operation switch. Besides, a control end of the startup switch is limited to one place of the device, but the position of the operation switch on the device can be selected from several positions, so that the operator can perform the restoration operation that restores the device from the sleep mode to the normal startup mode by the operation switch regardless of the position of the device. In this way, operability of the device can be improved.

According to the invention recited from technical solution 1 to technical solution 6, the path is provided which supplies electric power of the battery through the startup DC-DC converter to the startup circuit connection relay when the device is in the sleep mode, and input from the operation switch can be detected even when electric power is not supplied to a control circuit due to the startup switch is in the closing state and the switchgear is in the opening state. By such a configuration, the operator can easily perform the restoration operation that restores the device from the sleep mode to the normal startup mode by the operation switch without turning on/off the power source that operates the startup switch.

According to the invention recited in technical solution 2, the path is provided which supplies electric power of the battery through the startup DC-DC converter to the control circuit when the device is in the sleep mode, and the status indicator is made to display that the device is in the sleep mode. Thus, the operator can be informed that the device is in the sleep mode.

According to the invention recited in technical solution 3, the timer IC is arranged in the control circuit and display of the status indicator is controlled by the timer IC having an amount of power consumption less than that of the processor when the device is in the sleep mode, so that the operator can be informed that the device is in sleep mode with low consumed power without increasing the battery consumption in the sleep mode.

According to the invention recited in technical solution 4, the startup circuit can easily change a supply state of electric power supplied to an opening-closing relay that opens and closes the switchgear by switching a flow of current to the set coil side and reset coil side of the two-winding latching relay capable of self-holding.

According to the invention recited in technical solution 5, the startup switch is a key operation switch in which the contact point is opened and closed by operation of a key, so that the operator can manage electric power source of the device that generates X-rays by removing the key from the device when the device is not used.

According to the invention recited in technical solution 6 and technical solution 7, the operation switch includes any one of the brake lever arranged with the operation handle operating a traveling direction of the moving trolley the release button releasing fixation of the collimator position in the collimator that specifies an X-ray irradiation field in the X-ray irradiation part, the lighting button of the collimator lamp for confirming the X-ray irradiation field specified by the collimator, and the bumper switch detecting that the bumper arranged on the front surface of the moving trolley collides with an obstacle. Therefore, the operator can perform the restoration operation that restores the device from the sleep mode to the normal startup mode by switches in various parts of the device.

DESCRIPTION OF THE EMBODIMENTS

Figure 1:
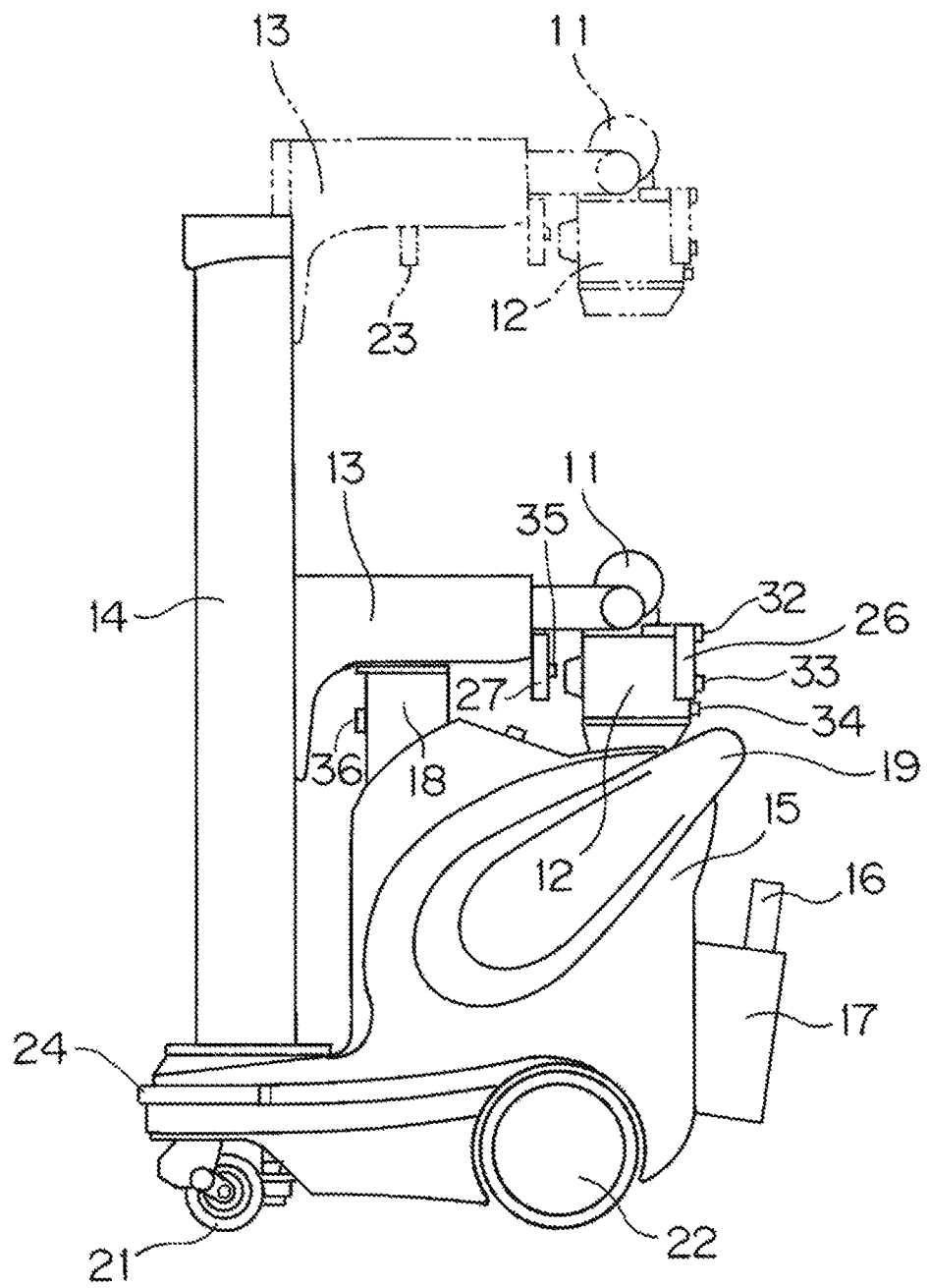
FIG. 1 is a side schematic view of a mobile X-ray imaging device of the disclosure.
Figure 2:
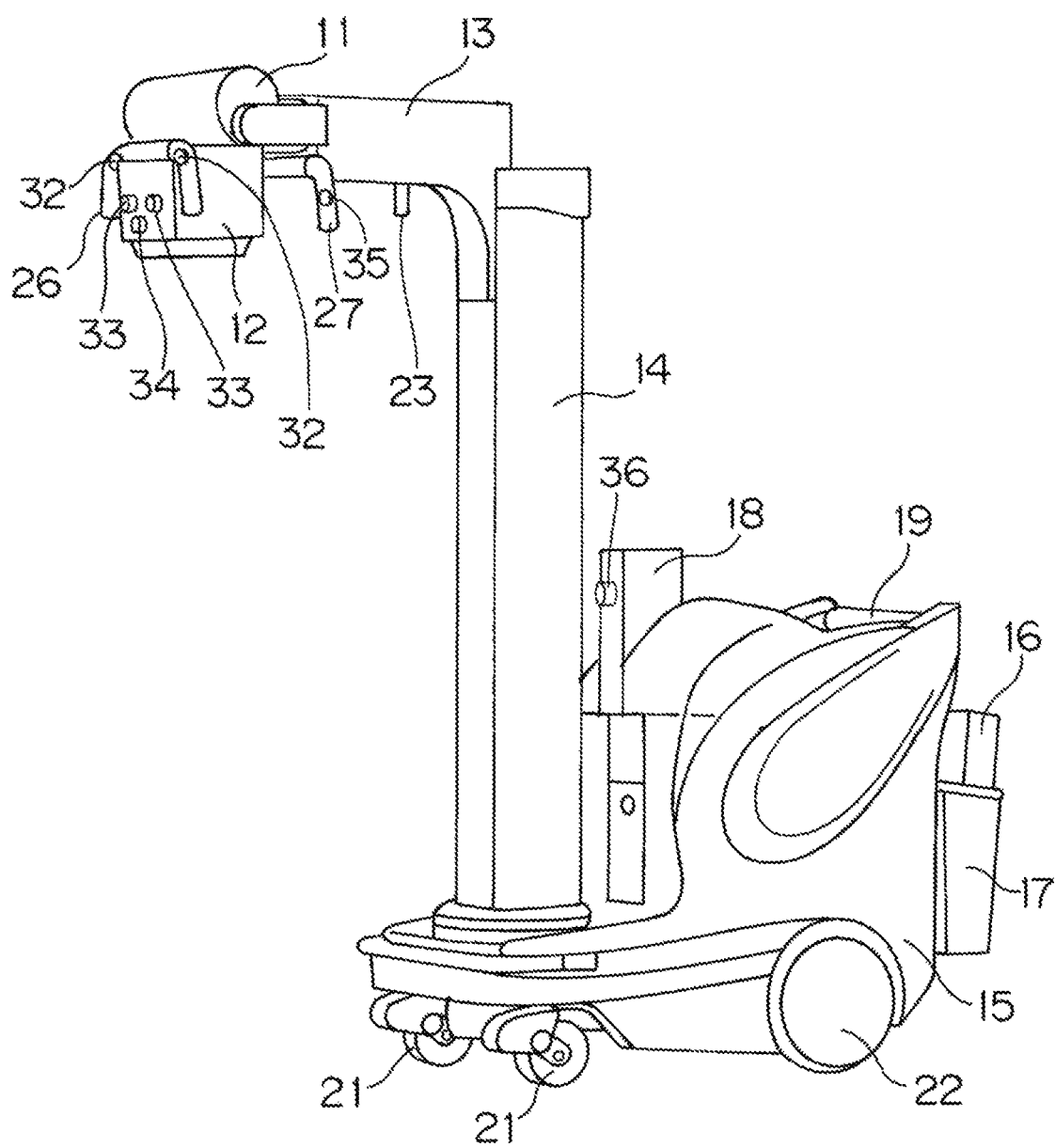
FIG. 2 is a perspective view of the mobile X-ray imaging device of the disclosure.
Figure 3:
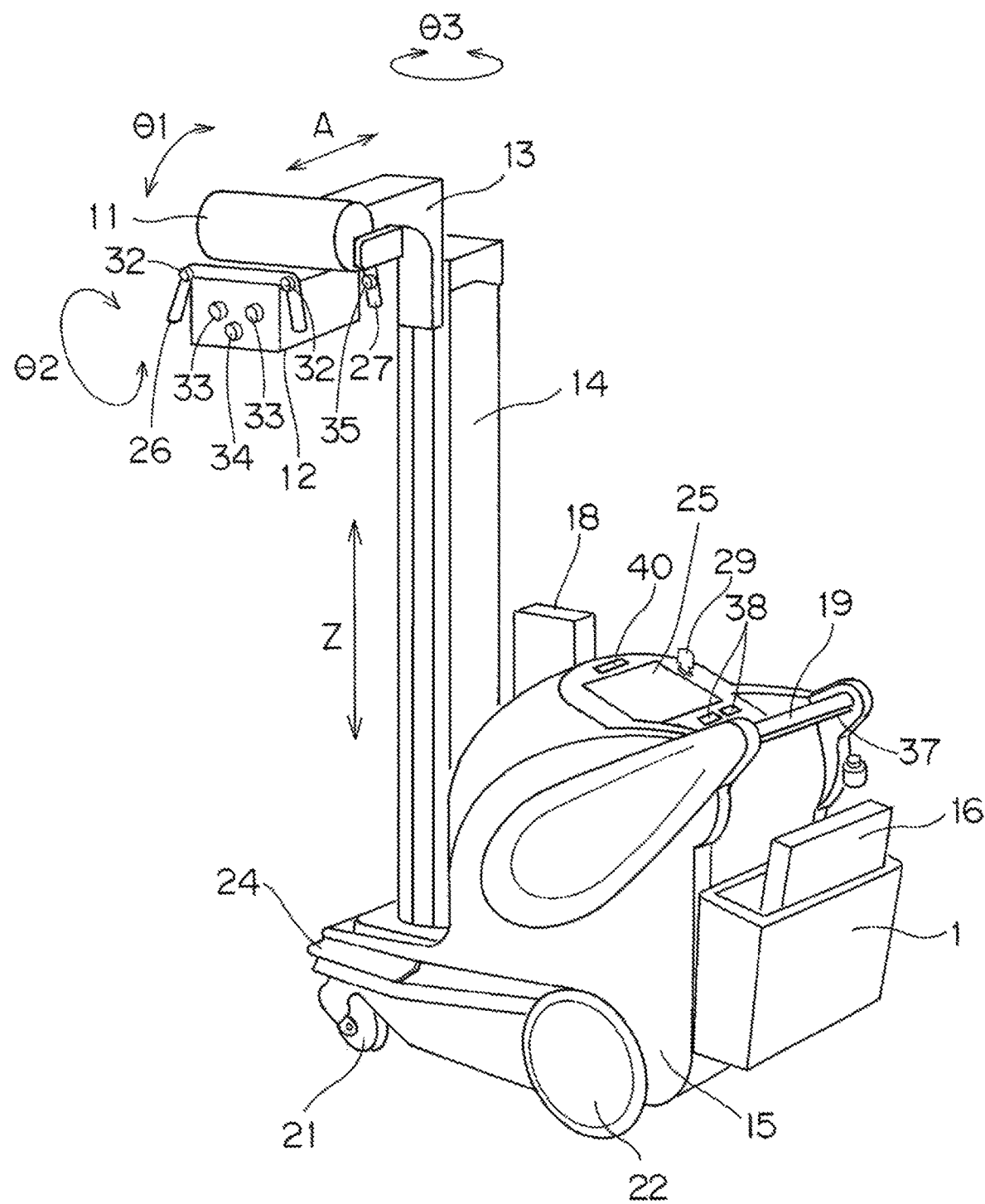
FIG. 3 is a perspective view of the mobile X-ray imaging device of the disclosure.

Embodiments of the disclosure is described below based on the drawings. FIG. 1 is a side schematic view of a mobile X-ray imaging device of the disclosure. Besides, FIG. 2 and FIG. 3 are perspective views of the mobile X-ray imaging device of the disclosure.

The mobile X-ray imaging device is equipped with elements required for movement of the device and X-ray imaging. The mobile X-ray imaging device includes a prop 14 arranged on a trolley 15, an arm 13 arranged to be liftable with respect to the prop 14, an X-ray tube 11 arranged on a leading end of the arm 13, a collimator 12 arranged below the X-ray tube 11, an X-ray detector 16 that detects X-rays irradiated from the X-ray tube 11 and passing through a subject, and an accommodation part 17 for accommodating the X-ray detector 16. The trolley 15 is a moving trolley provided with a pair of left and right front wheels 21 which are wheels for direction change and a pair of left and right rear wheels 22 which are wheels for driving, and a traveling direction of the trolley 15 is operated by an operation handle 19. Besides, a bumper 24 used to absorb an impact in a collision with an obstacle in the traveling direction is disposed in front of the trolley 15. Besides, together with the operation handle 19, a brake lever 37 (see FIG. 3) is arranged which performs fixation and fixation release using a brake on the rear wheels 22 by a grip of the operator.

The arm 13 is shown by a solid line in FIG. 1, and is capable of ascending and descending between a fixation position which is a position in which the arm 13 should be disposed when the trolley 15 is moved and an imaging position elevated from the fixation position. On the arm 13, a handle 27 is attached which is used when the arm 13 is lifted and lowered between the fixation position and the imaging position. In a state that the arm 13 is in the fixation position, a lower surface of the arm 13 is in contact with a fixation part 18 which is referred to as an arm catch. In this state, a pin 23 arranged on the lower surface of the arm 13 is accommodated and fixed in a hole part (not shown) formed in the fixation part 18. When the arm 13 is lifted from the fixation position to the imaging position, the operator operates a release button 36 attached to the fixation part 18 and releases the fixation of the pin 23. Besides, the arm 13 revolves, by rotating the prop 14, as shown in FIG. 3, in a 03 direction in a state of ascending from the fixation position.

Arranged on the front surface of the collimator 12 are a pair of dials 33 for opening and closing a collimator leaf specifying an X-ray irradiation field and a lighting button 34 for lighting a collimator lamp used to confirm the X-ray irradiation field. Besides, on the collimator 12, a handle 26 is attached which is used when moving the X-ray tube 11 and the collimator 12. Then, on the handle 26, a pair of release buttons 32 is attached which releases fixation of the arm 13 fixed by a fixation mechanism that prohibits lifting and revolution of the arm 13. Besides, a release button 35 having the same function as the release button 32 is also arranged on the handle 27 attached to the arm 13.

The X-ray tube 11 generating X-rays and the collimator 12 mounted on the X-ray tube 11 constitute an X-ray irradiation part and as shown in FIG. 3, are pivotable in a 01 direction centered on an axis facing a direction perpendicular to an extending direction of the arm 13 and a 02 direction centered on the axis facing the extending direction of the arm 13. Besides, as shown in FIG. 3, the X-ray tube 11 and the collimator 12 are movable in a horizontal direction due to the expansion and contraction of the arm 13 in an A direction. Furthermore, as shown in FIG. 3, the X-ray tube 11 and the collimator 12 are movable in a vertical direction due to the ascending and descending of the arm 13 with respect to the prop 14 in a Z direction.

Furthermore, the mobile X-ray imaging device is provided with a LCD touch panel 25 that functions as a display part and an operation part. On the LCD touch panel 25, operation switches for selecting imaging conditions or the like or X-ray photographed images or the like are displayed. Besides, around the LCD touch panel 25, for example, a setting switch 38 that can set the X-ray imaging conditions having a high frequency of use by one touch, a keyhole for the operator to insert a key 29 when turning power source of the device on/off, and a status indicator 40 showing a state of the device are disposed. In addition, the status indicator 40 is constituted by LED elements, and performs display by different light colors (yellow, blue, green, red and the like) corresponding to states in the X-ray irradiation such as a standby state in which preparations of the X-ray irradiation are completed.

Figure 4:
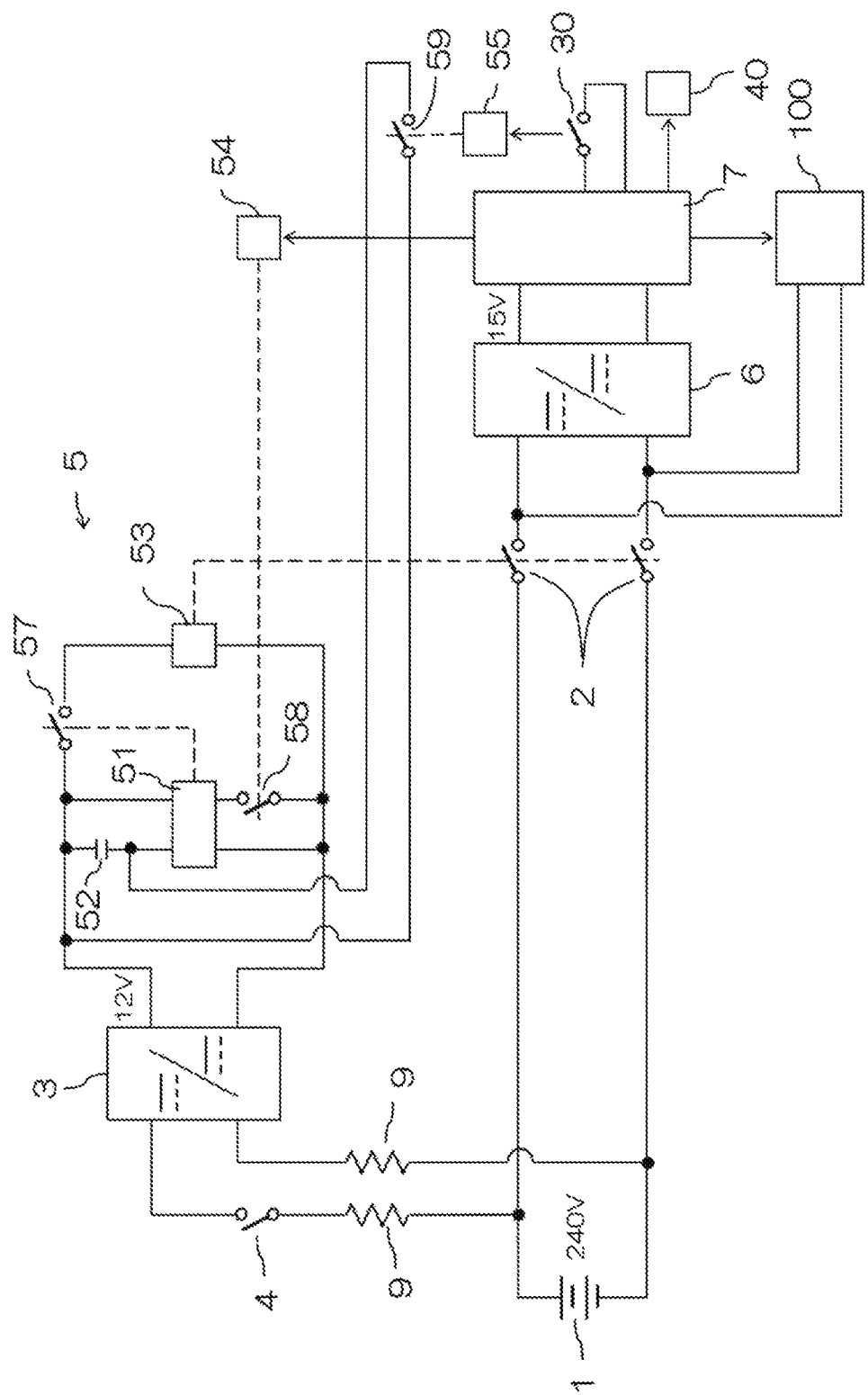
FIG. 4 is a circuit diagram illustrating a main electrical configuration of the mobile X-ray imaging device of the disclosure.
Figure 5:
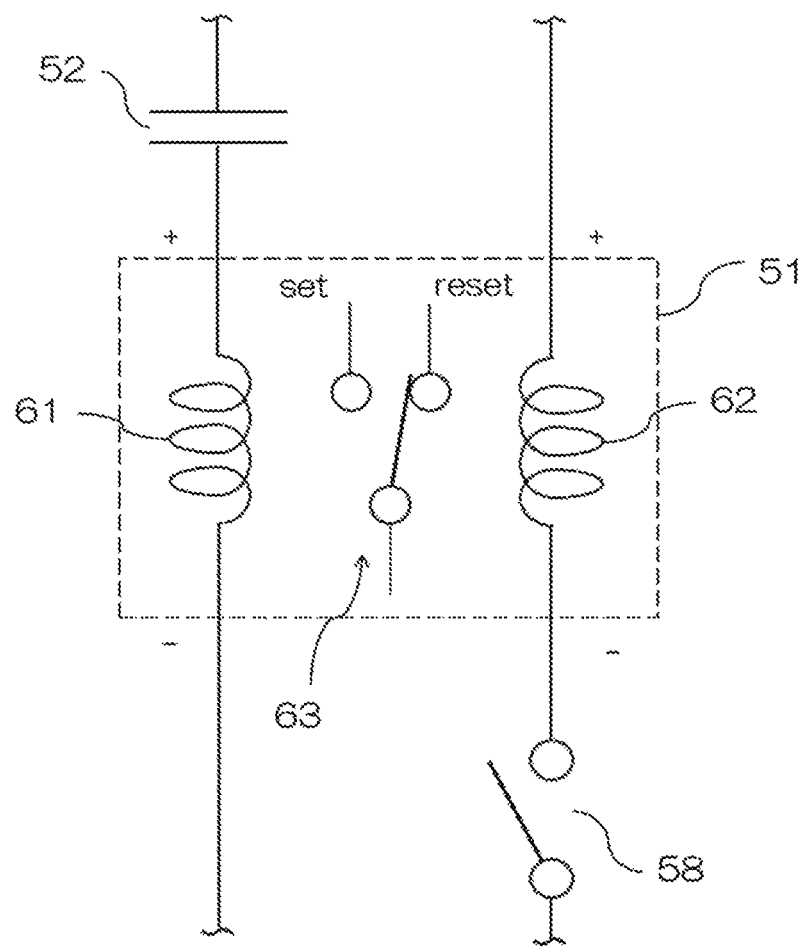
FIG. 5 is an illustration drawing of a latching relay 51.

FIG. 4 is a circuit diagram illustrating a main electrical configuration of the mobile X-ray imaging device of the disclosure. FIG. 5 is an illustration drawing of a latching relay 51.

Provided inside the trolley 15 are: a battery 1; a switchgear 2 arranged in a main path connecting a load 100 to the battery 1; a control circuit 7 that is connected, parallel to the load 100, to the main path for which connection to the battery 1 is switched by the switchgear 2 and that controls the load 100; a startup switch 4 which is a key operation switch that is opened and closed by operation of a key 29 by the operator; and a startup circuit 5 that is connected to the battery 1 and activates the switchgear 2 when the startup switch 4 is in the closing state. A protection resistor 9 is disposed in a path from the battery 1 to the startup circuit 5. Electric power supplied from the battery 1 to the startup circuit 5 is converted by a startup DC-DC converter 3 to a voltage (for example, 12 V) that activates the startup circuit 5. Besides, electric power supplied from the battery 1 to the control circuit 7 is converted by a control DC-DC converter 6 to a voltage (for example, 15 V) that activates the control circuit 7.

The startup circuit 5 includes an opening-closing relay 53 for opening and closing the switchgear 2 and a latching relay 51. The latching relay 51 is a two-winding latching relay and is a relay capable of self-holding that continues a state obtained by a set signal even after the set signal is excluded until a reset signal is given. A capacitor 52 is connected in series to a set coil 61 side of the latching relay 51 and a switch 58 is connected to a reset coil 62 side. The contact point 63 moves to the set side when the current flows to the set coil 61 side and the contact point 63 moves to the reset side when the current flows to the reset coil 62. Between the startup DC-DC converter 3 and the opening-closing relay 53, a switch 57 opened and closed by the latching relay 51 is arranged. Furthermore, the switch 58 is opened and closed by a mode transition relay 54, and the mode transition relay 54 operates in accordance with a command signal from the control circuit 7.

The control circuit 7 is provided with a processor that calculates operation signals of the elements connected to the control circuit 7. A plurality of operation switches for the operator to input an operation instruction to the device and various switches that input signals generated due to the operation of the operator are connected to the control circuit 7, for example, a brake lever 37, a release button 35 releasing fixation of the collimator position attached to the handle 27, a release button 36 attached to the fixation part 18, a lighting button 34 of a collimator lamp, and a bumper switch detecting that the bumper 24 collides with an obstacle. The operation switch 30 shown in FIG. 4 only shows one switch of a plurality of operation switches such as the brake lever 37, the release button 35, the release button 36, the lighting button 34, and the bumper switch. Besides, the status indicator 40 is connected to the control circuit 7.

Between the operation switch 30 and the startup circuit 5, a switch detection circuit is constituted which is provided with a startup circuit connection relay 55 that detects a signal when the operation switch 30 is in the closing state to activate the switch 59 connected parallel to the capacitor 52 of the startup circuit 5. That is, when any one switch of the brake lever 37, the release button 35, the release button 36, and the lighting button 34 is in the closing state, the switch 59 is activated by the startup circuit connection relay 55. The electric power to which voltage is converted by the startup DC-DC converter 3 is supplied via the startup circuit 5 to the switch detection circuit when the startup switch 4 is in the closing state and the switchgear 2 is in the opening state.

In an electric power supply circuit having such a structure, the electric power is supplied via the startup DC-DC converter 3 to the startup circuit 5 when the startup switch 4 is closed by operation of the operator. Accordingly, the charge current flows to the capacitor 52 and the current flows to the set coil 61 of the latching relay 51, thereby closing the switch 57, supplying the electric power to the opening-closing relay 53 and closing the switchgear 2. The switchgear 2 is closed and the electric power is supplied via the control DC-DC converter 6 to the control circuit 7, and thus the device comes into the normal startup mode.

In a case that there is no operation input from the operator for a fixed time when the startup switch 4 is in the closing state, the switchgear 2 is set to the opening state and the transition to the sleep mode with low power consumption is realized. That is, after a fixed time has elapsed since the startup switch 4 is in the closing state, an energization state of the opening-closing relay 53 in the startup circuit 5 is changed in accordance with a command of the control circuit 7.

When the input signal of any one of the plurality of operation switches 30 such as the brake lever 37, the release button 35, the release button 36, and the lighting button 34 connected to the control circuit 7 is not input to the control circuit 7 for a fixed time, the transition to the sleep mode is performed by way of sending signals to the mode transition relay 54 by the control circuit 7. According to the command signal from the control circuit 7, the mode transition relay 54 sets the switch 58 of the startup circuit 5 to the closing state. Accordingly, the current flows to the reset coil 62 of the latching relay 51, the contact point 63 switches to the reset side and the switch 57 is in the opening state. In this way, the energization to opening-closing relay 53 is blocked. Then, the switchgear 2 is in the opening state when the electric power of the opening-closing relay 53 is lost. By setting the switchgear 2 to the opening state, the connection of the battery 1 to the control circuit 7 and the load 100 is cut off and the device comes into the sleep mode. At this time, electric power is supplied to the startup circuit 5. At this time, electric power is not supplied to the control circuit 7, but electric power is supplied via the startup circuit 5 to the switch detection circuit that detects input of the operation switch 30.

When the operator operates any one of the plurality of operation switches 30 such as the brake lever 37, the release button 35, the release button 36, and the lighting button 34, the device restores from the sleep mode to the normal startup mode. If input of the operation switch 30 is detected and the startup circuit connection relay 55 operates, the switch 59 arranged in the path which supplies electric power from the startup circuit 5 to the switch detection circuit is in the closing state. In that case, the capacitor 52 of the startup circuit 5 is momentarily short-circuited, the current flows to the set coil 61 of the latching relay 51, and the contact point 63 switches to the set side. Accordingly, the switch 57 is closed and electric power is supplied to the opening-closing relay 53. If the energization state of the opening-closing relay 53 is changed again in this way, the switchgear 2 is in the closing state. If the switchgear 2 is in the closing state by restarting the energization to the opening-closing relay 53, the device restores to the normal startup mode in which the control circuit 7 receives supply of electric power from the battery 1 via the control DC-DC converter 6.

In the embodiment, when the operator restores the device from the sleep mode to the normal startup mode, a circuit structure is formed in which the supply of electric power is received from the startup circuit 5 to detect the input signal from the operation switch 30, and the opening-closing relay 53 in the startup circuit 5 is activated. Therefore, it is unnecessary to operate the key 29 to open and close the startup switch 4 as in the past. Besides, in this embodiment, electric power to which the voltage is converted by the startup DC-DC converter 3 is not supplied to the entire control circuit 7 via the startup circuit 5, and electric power is only supplied to the circuit that detects input of the operation switch 30. Therefore, consumed power of the sleep mode can be extremely reduced and consumption of the battery 1 can be suppressed. Furthermore, the input signal of the operation switch 30 may be the input signal from the bumper switch detecting that the bumper 24 collides with an obstacle.

Figure 6:
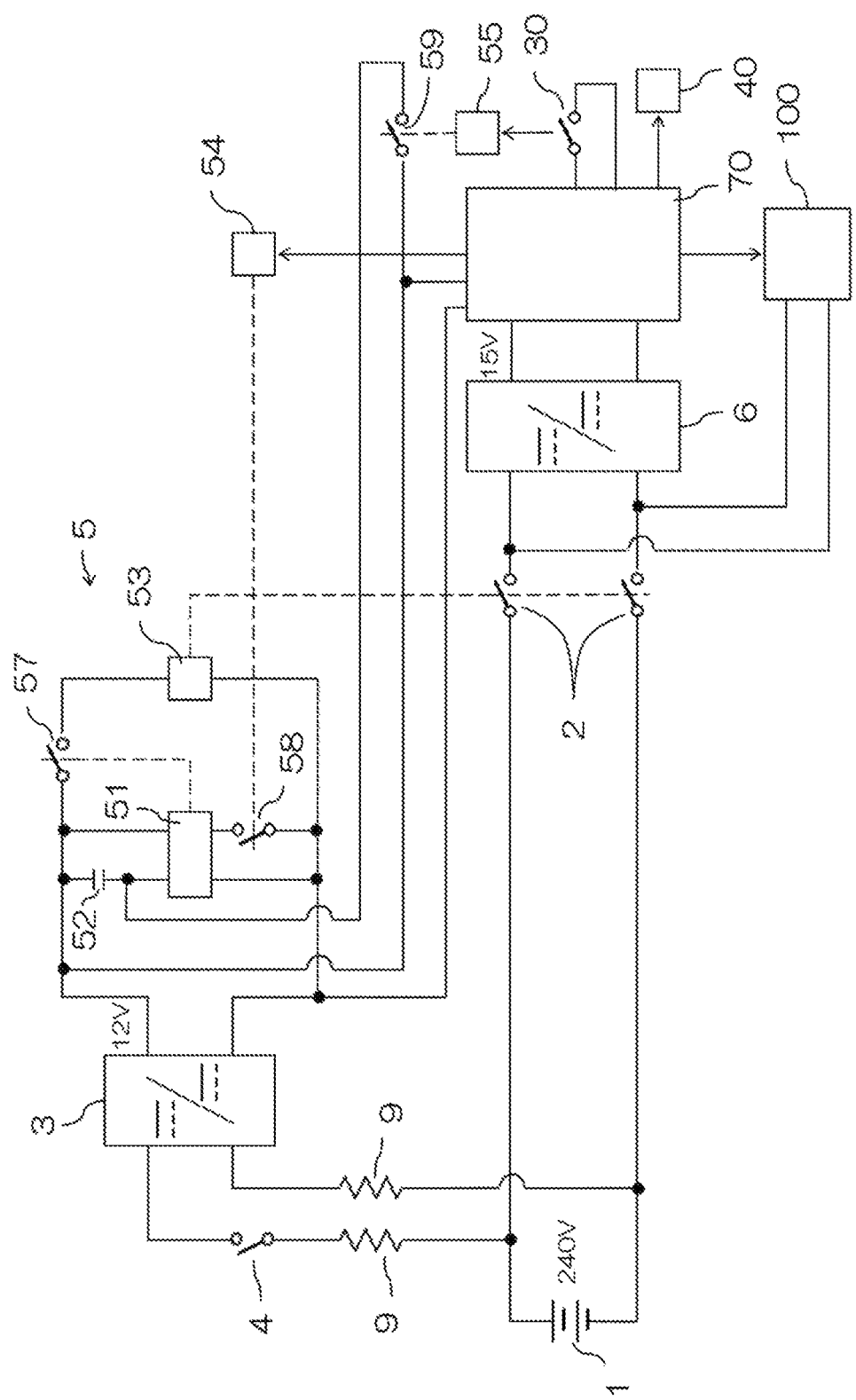
FIG. 6 is a circuit diagram illustrating a main electrical configuration of a mobile X-ray imaging device of the second embodiment.
Figure 7:
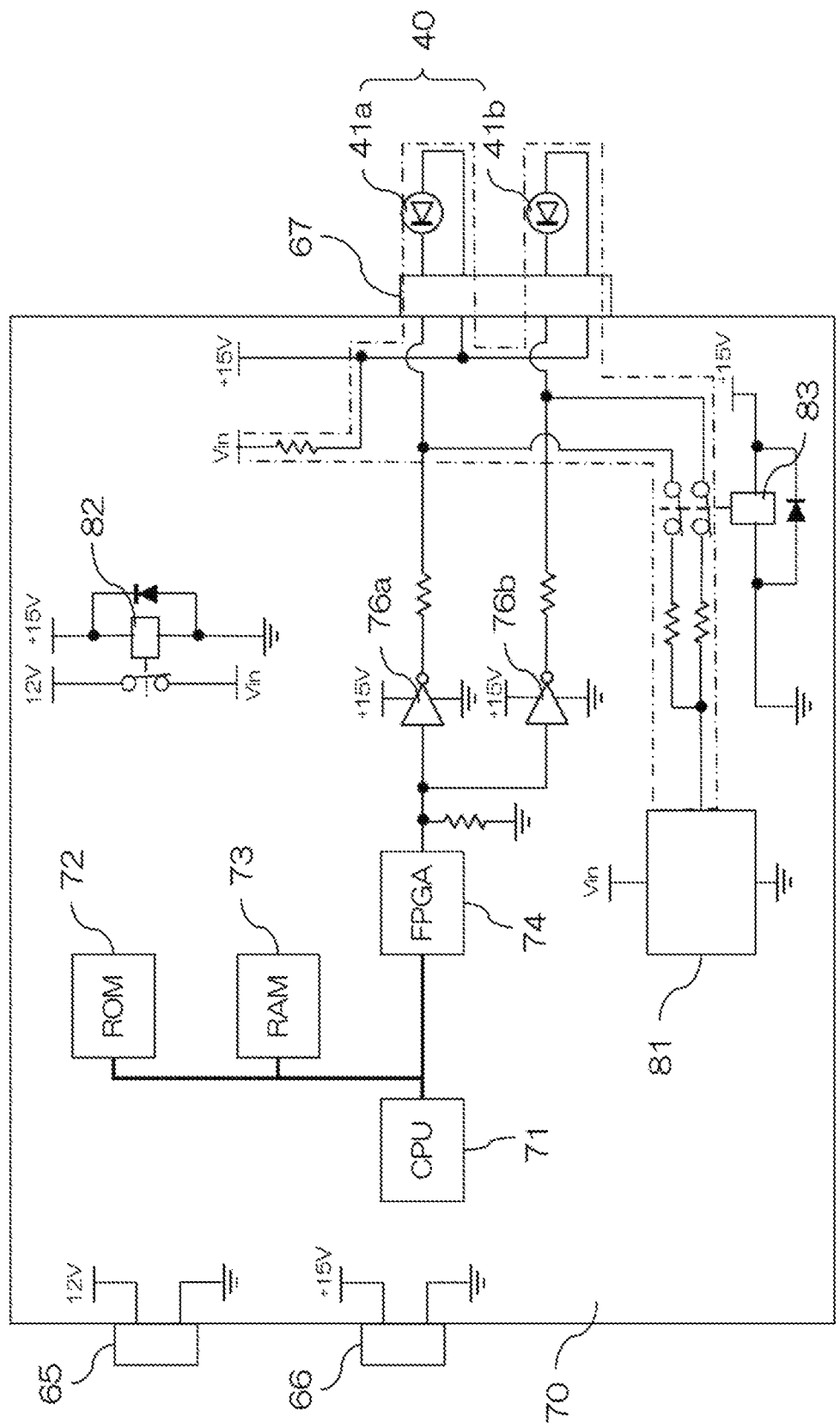
FIG. 7 is an illustration drawing showing an inner configuration of a control circuit 70.
Figure 8:
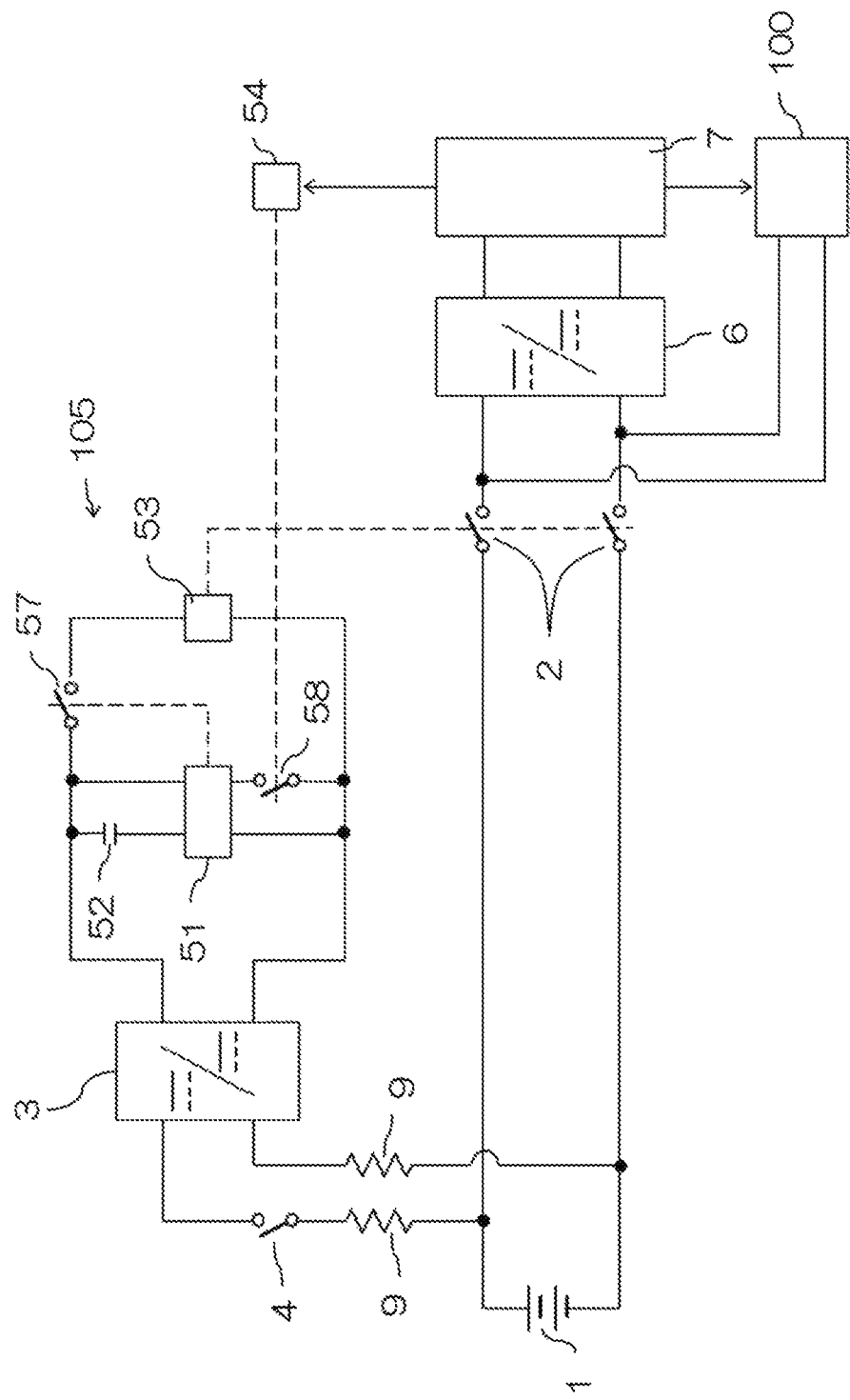
FIG. 8 is a circuit diagram illustrating a main electrical configuration of a conventional mobile X-ray imaging device.

FIG. 6 is a circuit diagram illustrating a main electrical configuration of the mobile X-ray imaging device of the second embodiment. FIG. 7 is an illustration drawing showing an inner structure of the control circuit 70.

In the electric power supply circuit shown in FIG. 6, a circuit structure is formed in which electric power is supplied from the startup circuit 5 to the entire control circuit 70 when the device is in the sleep mode, which is different from the first embodiment shown in FIG. 4. Structures equivalent to the first embodiment are denoted by the same reference numerals and specific descriptions thereof are omitted. The status indicator 40 is connected to the control circuit 70. A LED 41a and a LED 41b of FIG. 7 represent two of a plurality of light sources constituting the status indicator 40.

As shown in FIG. 7, the control circuit 70 includes a CPU 71, a ROM 72, a RAM 73, and a FPGA (Field-Programmable Gate Array) 74. The control circuit 70 receives, in the normal startup mode, electric power (15 V) from the control DC-DC converter 6 via the connector 66. Voltage which is suitable for each operation and which is converted, by the DC-DC converter which is not illustrated, from the voltage input from the control DC-DC converter 6 via the connector 66, is supplied to the CPU 71, the ROM 72, the RAM 73 and the FPGA 74. Besides, the LED 41a and the LED 41b constituting the status indicator 40 are connected via the connector 67 to the control circuit 70. The control circuit 70 includes a timer IC 81 that receives the supply of electric power via the startup DC-DC converter 3 when the device is in the sleep mode, and causes the status indicator 40 to display that the device is in the sleep mode.

In the normal startup mode, a flashing control of the LED 41a and the LED 41b in the status indicator 40 is performed by the CPU 71 via the FPGA 74 and a NOT circuit 76a and a NOT circuit 76b using a transistor. In the normal startup mode, a control command can be sent to the status indicator 40 by the CPU 71, so that control of a high degree of freedom can be performed, such as a change of display color, a switching of lighting and flashing of each LED, a change of flashing cycle, and a change of illuminance.

At this time, electric power (15 V) is also supplied from the control DC-DC converter 6 to a relay 82 shown in FIG. 7, and thus an electric power supply path from the startup DC-DC converter 3 via the connector 65 is in the opening state and electric power (12 V) is not supplied to Vin. Therefore, electric power is not supplied to the timer IC 81 and the timer IC 81 does not operate. Besides, electric power (15 V) is also supplied from the control DC-DC converter 6 to a relay 83 shown in FIG. 7, and thus a path from the timer IC 81 to the LED 41a and LED 41b is also in the opening state. Furthermore, a diode for consuming a surge current and protecting the circuit is connected in parallel with the relay coil to the relay 82 and the relay 83.

On the other hand, the switchgear 2 is in the opening state in the sleep mode, and thus electric power is not supplied from the control DC-DC converter 6 to the control circuit 70, and the CPU 71, the ROM 72, the RAM 73 and the FPGA 74 do not operate. Electric power is also not supplied from the control DC-DC converter 6 to the relay 82, and thus the electric power supply path from the startup DC-DC converter 3 is in a short-circuit state and electric power (12 V) is supplied to Vin. Therefore, the timer IC 81 receives a supply of electric power (12 V) from the startup DC-DC converter 3 and operates. Besides, electric power is not supplied from the control DC-DC converter 6 to the relay 83, and thus the path (shown by a one-dot dashed line in FIG. 7) from the timer-IC 81 to the LED 41a and the LED 41b is in a short-circuit state. In this way, the status indicator 40 is controlled by the timer IC 81.

The control of the status indicator 40 by the timer IC 81 is, for example, a flashing in a fixed cycle in which the LED 41a and the LED 41b are repeatedly turned on for one second and turned off for two seconds. By driving the LED 41a and the LED 41b in such a flashing cycle, the operator can be informed that the device is in the sleep mode.

In the control using the timer IC 81, a freedom degree of display of the status indicator 40 is lower than that of the control using the CPU 71, but device power consumption of the timer IC 81 is very low compared to the CPU 71. In this embodiment, when the device is in the sleep mode, a display that the device is in the sleep mode can be realized in low electric power by starting the timer IC 81 without starting the CPU 71 in the control circuit 70, so that consumed power of the battery 1 can be suppressed.

What is claimed is:

1. A mobile X-ray imaging device, on a moving trolley of which is equipped with an X-ray irradiation part having an X-ray tube for generating X-rays, an X-ray detector detecting the X-rays, a battery, and an electric power supply circuit for supplying electric power stored in the battery to a load, the mobile X-ray imaging device comprising:
a startup switch that opens and closes a supply path of electric power from the battery by operation of an operator;
a switchgear arranged in a main path of electric power supply from the battery to the load;
a startup circuit that has an opening-closing relay of the switchgear and sets the mobile X-ray imaging device to a normal startup mode by receiving the supply of electric power from the battery and setting the switchgear to a closing state when the startup switch is in a closing state;
a startup DC-DC converter converting a voltage of the electric power supplied from the battery to a voltage that activates the startup circuit;
a control circuit that receives the supply of electric power from the battery when the switchgear is in the closing state and that includes a processor calculating an operation signal of the mobile X-ray imaging device;
a control DC-DC converter converting the voltage of electric power supplied from the battery to a voltage that activates the control circuit;
a mode transition relay that changes an energization state of the opening-closing relay in the startup circuit according to a command of the control circuit after a fixed time has elapsed since the startup switch is in the closing state, thereby the switchgear is set to the opening state and the mobile X-ray imaging device is set to a sleep mode;
an operation switch that is connected to the control circuit and inputs an operation instruction to the mobile X-ray imaging device; and
a startup circuit connection relay that detects input from the operation switch and operates by receiving the supply of electric power from the startup DC-DC converter through the startup circuit when the mobile X-ray imaging device is in the sleep mode; wherein
in a case that the startup circuit connection relay detects input of the operation switch and operates when the mobile X-ray imaging device is in the sleep mode, the startup circuit changes the energization state of the opening-closing relay again to set the switchgear to the closing state and restores the mobile X-ray imaging device from the sleep mode to the normal startup mode.

2. The mobile X-ray imaging device according to claim 1, wherein
a status indicator for displaying a state of the mobile X-ray imaging device is connected to the control circuit, and
the control circuit receives the supply of electric power through the startup DC-DC converter when the mobile X-ray imaging device is in the sleep mode and causes the status indicator to display the sleep mode.

3. The mobile X-ray imaging device according to claim 2, wherein
the control circuit comprises a timer IC, and controls display of the status indicator by the processor in the normal startup mode and controls display of the status indicator by the timer IC in the sleep mode.

4. The mobile X-ray imaging device according to claim 1, wherein
the startup circuit comprises a two-winding latching relay and a capacitor connected in series to a set coil in the two-winding latching relay.

5. The mobile X-ray imaging device according to claim 1, wherein
the startup switch is a key operation switch in which a contact point is opened and closed by operation of a key.

6. The mobile X-ray imaging device according to claim 1, wherein
the operation switch comprises any one of a brake lever arranged with an operation handle operating a traveling direction of the moving trolley, a release button releasing fixation of a collimator position in a collimator that specifies an X-ray irradiation field in the X-ray irradiation part, a lighting button of a collimator lamp for confirming the X-ray irradiation field specified by the collimator, and a bumper switch detecting that a bumper arranged on a front surface of the moving trolley collides with an obstacle.

7. A mobile X-ray imaging device, on a moving trolley of which is equipped with an X-ray irradiation part having an X-ray tube for generating X-rays, an X-ray detector detecting the X-rays, a battery, and an electric power supply circuit for supplying electric power stored in the battery to a load, the mobile X-ray imaging device comprising:
a startup switch that opens and closes a supply path of electric power from the battery by operation of an operator;
a switchgear arranged in a main path of electric power supply from the battery to the load;

a startup circuit that has an opening-closing relay of the switchgear and sets the mobile X-ray imaging device to a normal startup mode by receiving the supply of electric power from the battery and setting the switchgear to a closing state when the startup switch is in a closing state;

a startup DC-DC converter converting a voltage of the electric power supplied from the battery to a voltage that activates the startup circuit;

a mode transition relay that blocks energization to the opening-closing relay in the startup circuit after a fixed time has elapsed since the startup switch is in the closing state, thereby the switchgear is set to an opening state and the mobile X-ray imaging device is set to a sleep mode; and a startup circuit connection relay that operates by receiving the supply of electric power from the startup DC-DC converter through the startup circuit when the mobile X-ray imaging device is in the sleep mode; wherein in a case that the startup circuit connection relay detects input from an operation switch and operates when the mobile X-ray imaging device is in the sleep mode, the startup circuit restarts the energization to the opening-closing relay to set the switchgear to the closing state and restores the mobile X-ray imaging device from the sleep mode to the normal startup mode; and the operation switch is any one of a brake lever arranged with an operation handle operating a traveling direction of the moving trolley, a release button releasing fixation of a collimator position in a collimator that specifies an X-ray irradiation field in the X-ray irradiation part, a lighting button of a collimator lamp for confirming the X-ray irradiation field specified by the collimator, and a bumper switch detecting that a bumper arranged on a front surface of the moving trolley collides with an obstacle.

* * * * *